United States Patent
Hartley et al.

(10) Patent No.: US 7,479,114 B2
(45) Date of Patent: Jan. 20, 2009

(54) DETERMINING BLOOD GAS SATURATION BASED ON MEASURED PARAMETER OF RESPIRATION

(75) Inventors: Jesse W. Hartley, Lino Lakes, MN (US); Jeffrey Stahmann, Ramsey, MN (US); Kent Lee, Fridley, MN (US); Quan Ni, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 438 days.

(21) Appl. No.: 11/291,480

(22) Filed: Dec. 1, 2005

(65) Prior Publication Data

US 2007/0129645 A1    Jun. 7, 2007

(51) Int. Cl.
    *A61B 5/08* (2006.01)
(52) U.S. Cl. ..................................... 600/529
(58) Field of Classification Search ................. 600/529, 600/532
    See application file for complete search history.

(56) References Cited

U.S. PATENT DOCUMENTS

| | | | |
|---|---|---|---|
| 4,562,841 A | 1/1986 | Brockway |
| 5,036,849 A | 8/1991 | Hauck |
| 5,156,157 A | 10/1992 | Valenta |
| 5,188,106 A | 2/1993 | Nappholz |
| 5,203,348 A | 4/1993 | Dahl |
| 5,284,136 A | 2/1994 | Hauck |
| 5,313,953 A | 5/1994 | Yomtov |
| 5,360,442 A | 11/1994 | Dahl |
| 5,366,496 A | 11/1994 | Dahl |
| 5,388,578 A | 2/1995 | Yomtov |
| 5,391,200 A | 2/1995 | KenKnight |
| 5,397,342 A | 3/1995 | Heil |
| 5,411,031 A | 5/1995 | Yomtov |
| 5,540,727 A | 7/1996 | Tockman |
| 5,545,202 A | 8/1996 | Dahl |
| 5,603,732 A | 2/1997 | Dahl |
| 5,836,987 A | 11/1998 | Baumann |
| 5,916,243 A | 6/1999 | KenKnight |
| 6,044,298 A | 3/2000 | Salo |
| 6,055,454 A | 4/2000 | Heemels |
| 6,126,611 A | 10/2000 | Bougeois |
| 6,270,457 B1 | 8/2001 | Bardy |
| 6,303,270 B1 | 10/2001 | Naim |
| 6,306,088 B1 | 10/2001 | Krausman |
| 6,312,378 B1 | 11/2001 | Bardy |
| 6,336,903 B1 | 1/2002 | Bardy |
| 6,398,728 B1 | 6/2002 | Bardy |

(Continued)

OTHER PUBLICATIONS

U.S. Appl. No. 10/643,006, filed Feb. 24, 2005, Lovett.

(Continued)

*Primary Examiner*—Charles A Marmor, II
*Assistant Examiner*—Christian Y Jang
(74) *Attorney, Agent, or Firm*—Hollingsworth & Funk, LLC (57) ABSTRACT

Systems and methods provide for determining blood gas saturation based on one or more measured respiration parameters. A parameter of respiration is measured implantably over a duration of time. The measured respiratory parameter is associated with a blood gas saturation level. Blood gas saturation is determined based on the measured respiration parameter. At least one of associating the measured respiratory parameter and determining blood gas saturation is preferably preformed implantably.

27 Claims, 9 Drawing Sheets

U.S. PATENT DOCUMENTS

| | | |
|---|---|---|
| 6,409,675 B1 | 6/2002 | Turcott |
| 6,450,957 B1 * | 9/2002 | Yoshimi et al. ............. 600/309 |
| 6,574,507 B1 | 6/2003 | Bonnet |
| 6,589,188 B1 | 7/2003 | Street |
| 6,600,949 B1 | 7/2003 | Turcott |
| 6,704,590 B2 | 3/2004 | Haldeman |
| 6,892,095 B2 | 5/2005 | Salo |

OTHER PUBLICATIONS

U.S. Appl. No. 10/309,770, filed Jun. 10, 2004, Ni.
U.S. Appl. No. 10/309,771, filed Jun. 10, 2004, Ni.
U.S. Appl. No. 10/643,016, filed Feb. 24, 2005, Stahmann.
U.S. Appl. No. 10/462,001, filed Nov. 18, 2004, Lovett.
U.S. Appl. No. 10/465,520, filed Nov. 18, 2004, Lindstrom.
U.S. Appl. No. 10/785,431, filed Jan. 6, 2005, Sanders.
U.S. Appl. No. 10/821,248, filed Oct. 28, 2004, Lovett.
U.S. Appl. No. 10/930,088, filed Aug. 31, 2004.
Satoh et al., "Role of Hypoxic Drive in Regulation of Postapneic Ventilation During Sleep in Patents with Obstructive Sleep Apnea", Am Rev Respir Dis, Mar. 1991 143(3): 481-485.

* cited by examiner

DETERMINING BLOOD GAS SATURATION BASED ON MEASURED PARAMETER OF RESPIRATION

FIELD OF THE INVENTION

The present invention relates generally to medical systems and methods, and more particularly, to medical systems and methods that determine blood gas saturation based on a measured parameter of respiration.

BACKGROUND OF THE INVENTION

Disordered breathing refers to a wide spectrum of respiratory conditions that involve disruption of the normal respiratory cycle. Although disordered breathing typically occurs during sleep, the condition may also occur while the patient is awake. Unfortunately, disordered breathing is often undiagnosed. If left untreated, the effects of disordered breathing may result in serious health consequences for the patient.

Apnea is a fairly common breathing disorder characterized by periods of interrupted breathing. Apnea is typically classified based on its etiology. One type of apnea, denoted obstructive apnea, occurs when the patient's airway is obstructed by the collapse of soft tissue in the rear of the throat. Central apnea is caused by a derangement of the central nervous system control of respiration. The patient ceases to breathe when control signals from the brain to the respiratory muscles are absent or interrupted. Mixed apnea is a combination of the central and obstructive apnea types. Regardless of the type of apnea, people experiencing an apnea event stop breathing for a period of time. The cessation of breathing may occur repeatedly during sleep, sometimes hundreds of times a night and sometimes for a minute or longer.

In addition to apnea, other types of disordered respiration have been identified, including hypopnea (shallow breathing), tachypnea (rapid breathing), hyperpnea (heavy breathing), and dyspnea (labored breathing). Combinations of the respiratory cycles described above may be observed, including, for example, periodic breathing and Cheyne-Stokes respiration (CSR). Periodic breathing is characterized by cyclic respiratory patterns that may exhibit rhythmic rises and falls in tidal volume. Cheyne-Stokes respiration is a specific form of periodic breathing wherein the tidal volume decreases to zero resulting in apneic intervals. The breathing interruptions of periodic breathing and CSR may be associated with central apnea, or may be obstructive in nature. CSR is frequently observed in patients with congestive heart failure (CHF) and is associated with an increased risk of accelerated CHF progression.

Disordered breathing episodes can contribute to changes in a patient's blood gas saturation. Blood oxygen saturation decreases when the number of oxygen binding sites in a patient's blood stream remaining unfilled increases. Similarly, blood carbon dioxide saturation increases when carbon dioxide is no longer being exchanged when ventilation decreases or stops. Less oxygen is delivered to the blood stream and the rate of carbon dioxide exchange decreases during periods of disordered breathing resulting in a decrease of blood oxygen saturation and an increase in carbon dioxide saturation. As a result, disordered breathing can have cardiovascular implications such as the development of systemic hypertension and thus detection of respiration-related disorders affecting patient blood gas saturation is of particular interest.

SUMMARY OF THE INVENTION

The present invention is directed to systems and methods for determining blood gas saturation based on one or more measured respiration parameters. Embodiments of the present invention involve implantably measuring a parameter of respiration over a duration of time, associating the measured respiratory parameter with a blood gas saturation level, and determining blood gas saturation based on the measured respiration parameter. At least one of associating the measured respiratory parameter and determining blood gas saturation is preferably performed implantably. Blood gases of interest include blood oxygen and blood carbon dioxide.

The parameter of respiration may include one or both of a magnitude and a frequency of change in transthoracic impedance. Other parameters of respiration may include at least one of a respiration pattern, a respiration interval, tidal volume, and minute ventilation. Further parameters of respiration may include at least of a duration of an apnea episode, a duration of a hypopnea episode, and a duration of a Cheyne-Stokes respiration episode. The parameter of respiration may include a frequency of respiration during a disordered breathing event or a frequency of respiration before or after a disordered breathing event.

Implantably measuring the parameter of respiration may involve implantably measuring a baseline parameter of respiration during patient wakefulness. Determining blood gas saturation may involve determining blood gas saturation during sleep. Embodiments of the present invention may involve detecting sleep disordered breathing, and indicating a severity level of the sleep disordered breathing in response to detecting sleep disordered breathing with a presence or absence of a change in blood gas saturation.

Embodiments of the present invention may involve measuring one or more of a cardiac parameter, blood pressure parameter and blood flow parameter. Determining blood gas saturation may be based at least in part on one or more of the cardiac parameter, blood pressure parameter and blood flow parameter. Determining blood oxygen saturation, for example, may involve indicating a decrease in blood oxygen saturation in response to measuring a decrease in at least one of a respiratory tidal volume, a minute ventilation, and a respiration rate. Determining blood oxygen saturation may also involve indicating a decrease in blood oxygen saturation in response to measuring an increase in sleep disordered breathing episodes.

Determining blood carbon dioxide saturation, for example, may involve indicating an increase in blood carbon dioxide saturation in response to measuring a decrease in at least one of a respiratory tidal volume, a minute ventilation, and a respiration rate. Determining blood carbon dioxide saturation may also involve indicating an increase in blood carbon dioxide saturation in response to measuring an increase in sleep disordered breathing episodes.

According to other embodiments of the present invention, systems for measuring parameters indicative of blood gas saturation include an implantable device configured to measure a parameter of respiration over a duration of time. A processor is configured to associate the measured respiratory parameter with a blood gas saturation level, and to determine blood gas saturation based on the measured respiration parameter. The processor may be disposed in an implantable housing.

The processor may be configured to detect one or both of a magnitude and frequency of change in transthoracic impedance. The system may include a sensor configured to measure a cardiac parameter, and the processor may be configured to associate the cardiac parameter with a blood gas saturation level and to determine blood gas saturation based at least in part on the measured cardiac parameter.

The system may include a sensor configured to measure a blood pressure or blood flow parameter, and the processor may be configured to associate the blood pressure or blood flow parameter with a blood gas saturation level and to determine blood gas saturation based at least in part on the measured blood pressure or blood flow parameter. The system may include a sensor configured to measure one or both of patient activity and patient posture, and the processor may be configured to determine or confirm blood gas saturation based at least in part on the measured one or both of patient activity and patient posture. The system may include a communication link configured to communicate the determined blood gas saturation values to a patient-external location.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which are shown by way of illustration, various embodiments by which the invention may be practiced. It is to be understood that other embodiments may be utilized, and structural and functional changes may be made without departing from the scope of the present invention.

In the past, a patient's blood oxygen or carbon dioxide saturation has been determined using photoplethysmography, which is a non-invasive method of measuring blood oxygen or carbon dioxide saturation. Conventional photoplethysmography usually requires a sensor to be placed on an extremity such as a finger, toe or earlobe. These sensors can produce unreliable results when blood flow to the extremities is reduced due to shock, cold temperature, vascular disease or patient movement, for example.

Patient-internal sensors that measure blood oxygen or carbon dioxide saturation can also be problematic and unreliable. In an implanted system, multiple sensors can sense different levels of blood gas saturation resulting in uncertain measurements. Furthermore, with an increased number of implanted sensors, the stability and reliability of an implanted device typically decreases and power consumption increases.

Blood gas saturation measurements can be used to adjust cardiac rhythm management (CRM) and/or positive airway pressure therapies to provide more effective treatment of disordered breathing, a pulmonary condition, and/or a cardiac condition. Positive airway pressure therapies include continuous positive airway pressure (CPAP) therapy, bi-level positive airway pressure (bi-PAP) therapy, proportional positive airway pressure (PPAP) therapy, and/or autotitration positive airway pressure therapy, for example. Various diseases and disorders, e.g., sleep apnea, are associated with various blood gas concentration levels. The detection of changes in blood gas saturation may be used in connection with diagnosis of a variety of diseases. Further, blood gas concentrations may be used to detect and/or predict episodes of disordered breathing, a pulmonary condition, and/or a cardiac condition. Further, blood gas concentrations may be used to initiate, terminate, or modify respiratory and cardiac therapy.

Embodiments of the present invention determine or predict the depth of oxygen and/or carbon dioxide saturation without requirement of unreliable and expensive external or internal blood oxygen/carbon dioxide sensors. In various embodiments of the invention, changes in blood oxygen and/or carbon dioxide saturation can be detected during periods of sleep disordered breathing, such as during apnea and hypopnea episodes. Blood oxygen and/or carbon dioxide saturation may be determined by processing respiratory signals acquired from an implantable transthoracic impedance sensor or other medical device capable of sensing patient respiratory characteristics. By determining the extent of low blood oxygen saturation and/or high carbon dioxide saturation during apnea/hypopnea episodes, for example, the potential effects of decreased blood oxygen saturation and/or increased carbon dioxide saturation on a patient may be better determined.

Figure 1:
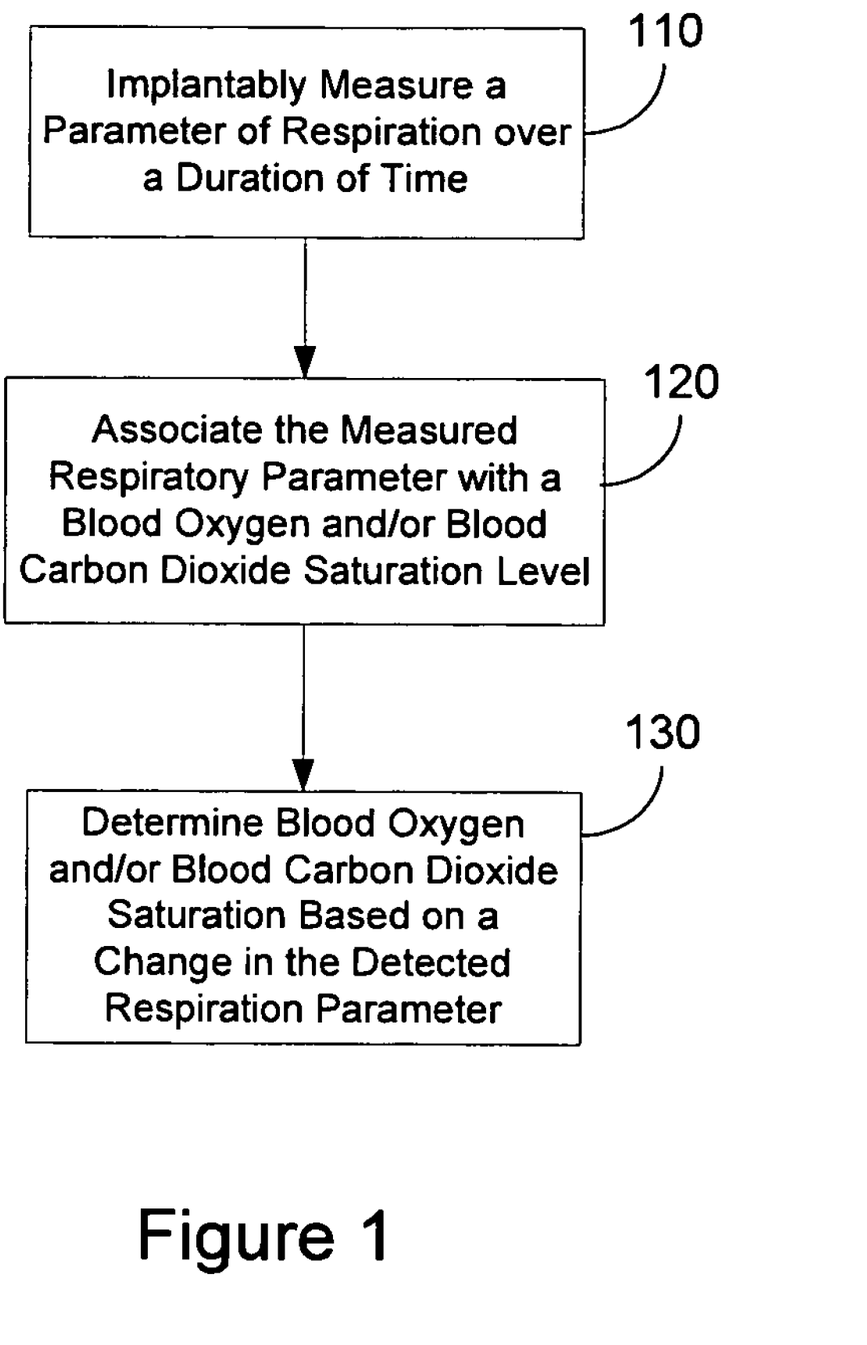
FIG. 1 is a flow chart illustrating a method for measuring blood gas saturation in accordance with embodiments of the present invention.

Referring to FIG. 1, a method for measuring one or more parameters indicative of blood gas saturation in accordance with embodiments of the invention is illustrated. The method includes implantably measuring 110 a parameter of respiration over a duration of time. The measured respiratory parameter is associated 120 with a blood oxygen and/or carbon dioxide saturation level. The blood oxygen and/or carbon dioxide saturation is determined 130 based on a change in the measured 110 respiratory parameter.

Figure 2:
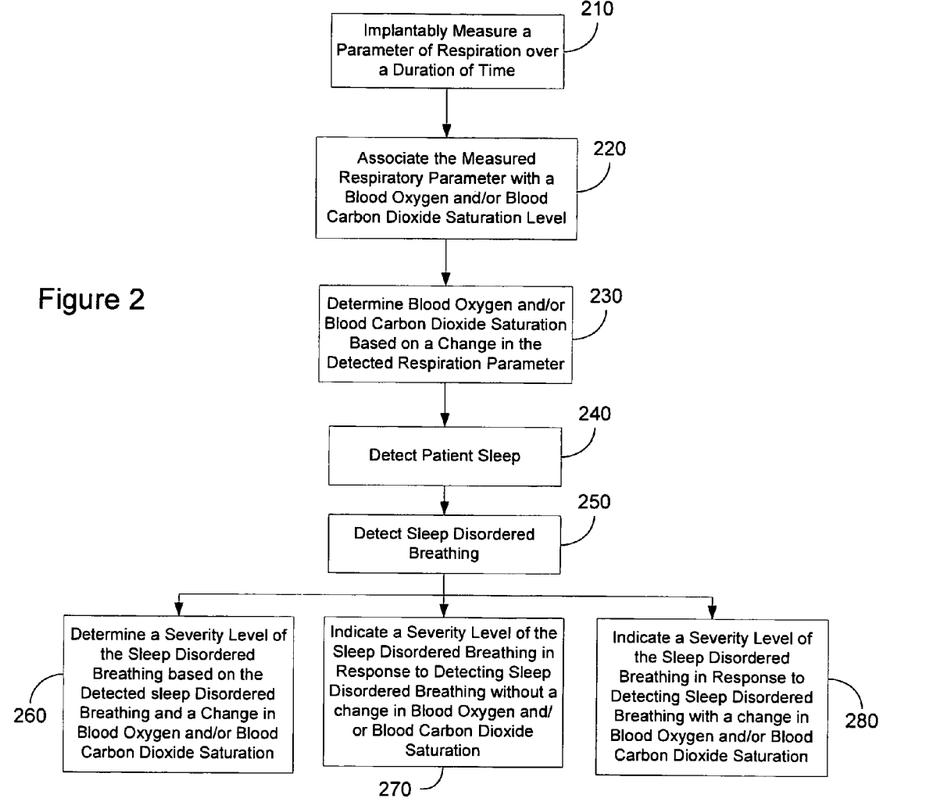
FIG. 2 is a more detailed flow chart illustrating a method for measuring blood gas saturation in accordance with embodiments of the present invention.

FIG. 2 is a more detailed illustration of a method for measuring parameters indicative of blood gas saturation in accordance with embodiments of the present invention. A parameter of respiration, such as transthoracic impedance, is implantably measured 210 over a period of time. Upon respiratory inspiration, transthoracic impedance increases, and upon respiratory expiration, transthoracic impedance decreases, thus allowing a frequency and/or magnitude of change in transthoracic impedance to be measured over time.

In further embodiments of the invention, parameters of respiration can be measured 210 by measuring a baseline parameter of respiration. For example, historical data of a patient's respiratory parameter can be used to generate a baseline parameter by graphing the historical data over a period of time. A baseline respiratory parameter can be established during certain periods of the day, such as during patient wakefulness.

A variety of respiratory characteristics can be implantably measured. For example, tidal volume can be measured as a magnitude of change in transthoracic impedance. A frequency of respiration before and during a disordered breathing event, and a duration of apnea, hypopnea, and/or Cheyne-Stokes respiration (CSR), can be measured by determining a frequency of change in a patient's transthoracic impedance. Minute ventilation (MV) can be determined from measuring a magnitude and frequency of change in transthoracic impedance. In accordance with embodiments of the invention, other respiratory parameters, such as respiration patterns and intervals can be detected. In addition, types of disordered breathing, such as apneas, including obstructive sleep apnea, central sleep apnea and hypopneas can also be detected as a respiratory parameter in accordance with embodiments of the invention.

Respiratory parameters are measured 210 over a period of time which may include one or more days, weeks or months. The information collected over the period of time can be used to trend respiratory parameter data, for example.

It should be understood that devices other than transthoracic impedance sensors can be used in connection with measuring respiratory parameters in accordance with embodiments of the present invention. For example, an accelerometer can be incorporated into an implantable device to measure chest wall movement and respiratory characteristics connected with chest wall movement. An accelerometer may also be used to detect changes in patient posture or patient activity.

Measured parameters of respiration are associated 220 with blood gas saturation levels, such as blood oxygen and/or carbon dioxide saturation levels. Respiratory parameters such as resting tidal volume, minute ventilation and/or respiratory rate during patient wakefulness are measured and/or trended, and can be associated 220 with times of changing blood gas saturation.

By way of example, periods of normal or high respiration may be associated over a long period of time with normal levels of oxygen saturation, at least in patients without severely compromised lung disease. By trending respiratory parameters, such as tidal volume or respiratory frequency, the periods where the tidal volume and respiratory rate are high can be associated with periods of normal oxygen saturation.

Once a reference oxygen saturation is determined or inferred, changes in oxygen saturation relative to the reference can be tracked.

By way of further example, the length of an apnea episode may be used to predict the degree of oxygen desaturation or carbon dioxide saturation. The duration and depth of hyperventilation (time, amplitude, and minute ventilation) may be used to determine the degree of oxygen re-saturation or carbon dioxide desaturation.

Blood oxygen and/or carbon dioxide saturation is then determined 230 based on the measured respiration parameter. For example, determining blood oxygen and/or carbon dioxide saturation can be a result of measuring tidal volume, minute ventilation, respiratory rate and/or apnea/hypopnea. Low measurements of tidal volume, minute ventilation and respiratory rate are indicative of a decrease in blood oxygen saturation and an increase of carbon dioxide saturation. As the measurements of occurrences of sleep disordered breathing such as apneas and hypopneas increases, blood oxygen saturation decreases and carbon dioxide increases. Similarly, the hyperventilation that follows an apnea or hypopnea episode will decrease blood carbon dioxide saturation and increase blood oxygen saturation. In embodiments of the invention, blood oxygen and/or carbon dioxide saturation can be determined 230 by trending the measurements of the above-mentioned characteristics over time.

Determination 230 of blood oxygen and/or carbon dioxide saturation can take place during certain times, such as during patient sleep. Sleep disordered breathing and blood oxygen and/or carbon dioxide saturation during sleep can be determined 250 once patient sleep is detected 240. A severity level of sleep disordered breathing can be determined 260 based on the measured characteristic indicative of blood oxygen and/or carbon dioxide saturation during sleep. The degree of severity of sleep disordered breathing can be dependent on whether the degree of change in the parameter of respiration increases or decreases over time. Techniques involving detecting sleep are described in commonly owned U.S. patent application having application Ser. No. 10/643,006 filed on Aug. 18, 2003, and entitled "Sleep State Classification," which is incorporated by reference herein in its entirety.

In alternative embodiments of the present invention, a severity of sleep disordered breathing can be indicated based on the detection 250 of sleep disordered breathing and the measured parameter of respiration associated with blood oxygen and/or carbon dioxide saturation. For example, sleep disordered breathing with a normal respiration parameter measurement that is indicative of a normal blood oxygen and/or carbon dioxide saturation may be indicative 270 of a less serious type of sleep disordered breathing and therefore is not as significant to a patient's prognosis. On the other hand, sleep disordered breathing with an abnormal respiration parameter measurement indicating low blood oxygen saturation and/or high carbon dioxide saturation may be indicative 280 of a more serious form of sleep disordered breathing that is medically significant. For example, blood oxygen saturation levels are clinically significant because hypoxia over time can be related to inflammatory processes that lead to hypertension.

In other embodiments of the present invention, additional parameters such as cardiac or blood pressure parameters can be measured. The measured cardiac or blood pressure parameters can be associated with a blood oxygen and/or carbon dioxide saturation level and may be used in addition to the measured parameter of respiration to determine blood oxygen and/or carbon dioxide saturation. For example, a measured increase in blood pressure can be indicative of a decrease in blood oxygen saturation when occurring with decreases in other respiratory parameters. Also, low oxygen saturation or hypoxia is associated with oxidative stress, which then releases hypertensive factors which cause vasoconstriction. These acute changes in blood pressure may be associated with intermittent drops in blood oxygen saturation.

In generally, hypoxia or a decrease in blood oxygen saturation are associated with an increase in blood pressure, both acute and chronic. An implantable blood pressure sensor, such as a sensor located in the right ventricle, can be used to measure an acute increase in blood pressure, which can improve the confidence that a decrease in respiratory parameters is indicative of a decrease in blood oxygen saturation, rather than a change in posture for example.

Posture is another useful parameter that can be measured. Determining patient posture may improve blood oxygen saturation determinations, such as by verifying that detected changes in respiratory parameters are indicative of changes in blood oxygen saturation, rather than changes in posture. Posture sensors such as those incorporating an accelerometer or other rate or tilt sensing devices, may be used.

Blood flow is also a useful parameter that can be measured, such as by use of a Doppler or other ultrasonic sensor. An increase in blood flow can be used in a manner similar to that associated with blood pressure, with an increase in blood flow indicating a decrease in blood oxygen saturation when occurring with decreases in other respiratory parameters. Examples of useful blood flow sensing techniques are disclosed in commonly owned U.S. Pat. Nos. 6,704,590 and 6,892,095, and in commonly owned U.S. application Ser. No. 10/930,088 filed Aug. 31, 2004, and further in U.S. Pat. Nos. 5,188,106 and 5,156,157, all of which are hereby incorporated herein by reference.

Any or all of the information collected and generated using methods for measuring respiratory parameters indicative of blood oxygen saturation can be recorded and stored for future use, such as for trending and predicting blood oxygen and/or carbon dioxide saturation.

Figure 3:
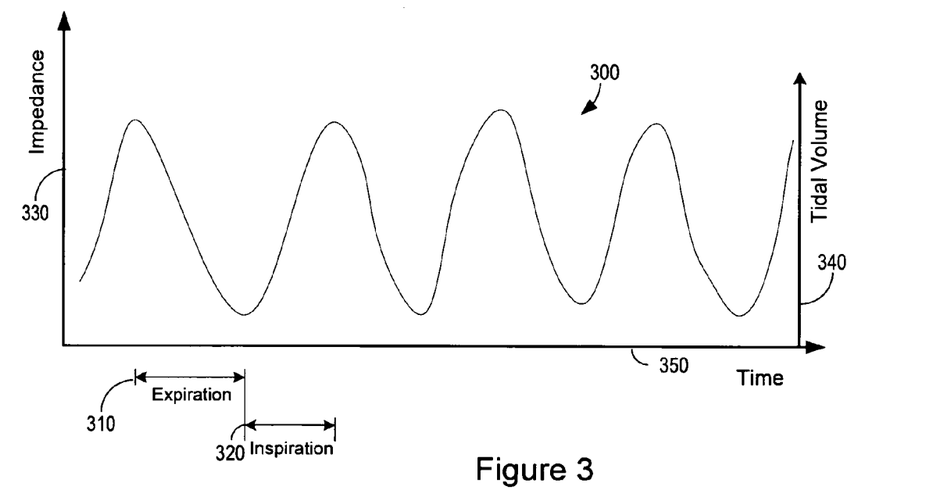
FIG. 3 is a graph of a normal respiration signal measured by a transthoracic impedance sensor that may be utilized for measuring blood gas saturation in accordance with embodiments of the present invention.

Referring now to FIG. 3, a non-filtered transthoracic impedance signal 300 is illustrated. The impedance signal 300 may be developed, for example, from an impedance sense electrode in combination with a patient internal medical device used in accordance with embodiments of the present invention. The impedance signal 300 is proportional to the transthoracic impedance, illustrated as impedance 330 on the abscissa of the left side of the graph in FIG. 3. The impedance 330 increases during any respiratory inspiration 320 and decreases during any respiratory expiration 310. The impedance signal 300 is also proportional to the amount of air inhaled, denoted a tidal volume 340, illustrated on the abscissa of the right side of the graph in FIG. 3.

The variations in impedance during respiration, identifiable as the peak-to-peak variation of the impedance signal 300, may be used to determine the respiration tidal volume 340, corresponding to the volume of air moved in a breath, one cycle of expiration 310 and inspiration 320. A minute ventilation may also be determined, corresponding to the amount of air moved per a minute of time 350 illustrated on the ordinate of the graph in FIG. 3. The impedance signal 300 would also show transient events, such as rales and/or coughs, to provide useful patient condition and prediction information. Any or all of the tidal volume 340 measurement, minute ventilation 350 and other events may be used for determining blood oxygen and/or carbon dioxide saturation in accordance with embodiments of the present invention.

Sleep disordered breathing disorders may be determined using the impedance signal 330. During non-REM sleep, a normal respiration pattern includes regular, rhythmic inspiration-expiration cycles without substantial interruptions. When the tidal volume (TV) of the patient's respiration, as indicated by the transthoracic impedance signal, falls below a hypopnea threshold, then a hypopnea event is declared. For example, a hypopnea event may be declared if the patient's tidal volume falls below about 50% of a recent average tidal volume or other baseline tidal volume value. If the patient's tidal volume falls further to an apnea threshold, e.g., about 10% of the recent average tidal volume or other baseline value, an apnea event is declared. Apnea and hypopnea events can also contribute to a decrease in a patient's blood oxygen saturation and an increase in blood carbon dioxide saturation, and thus can be used to determine a patient's blood oxygen/carbon dioxide saturation in accordance with embodiments of the present invention.

Figure 4:
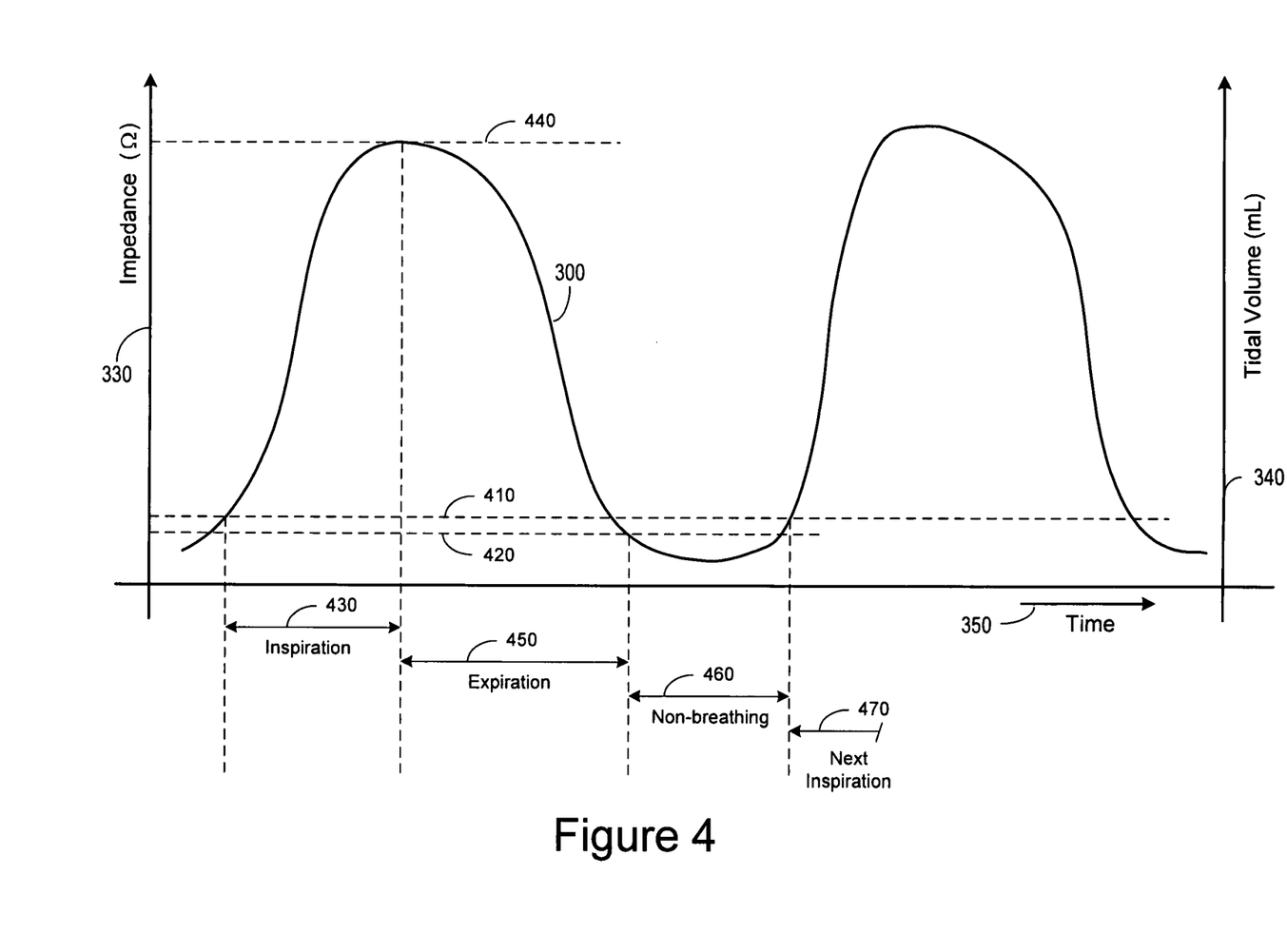
FIG. 4 is a respiration signal graph illustrating respiration intervals used for disordered breathing detection and/or prediction according to embodiments of the invention.
Figure 5:
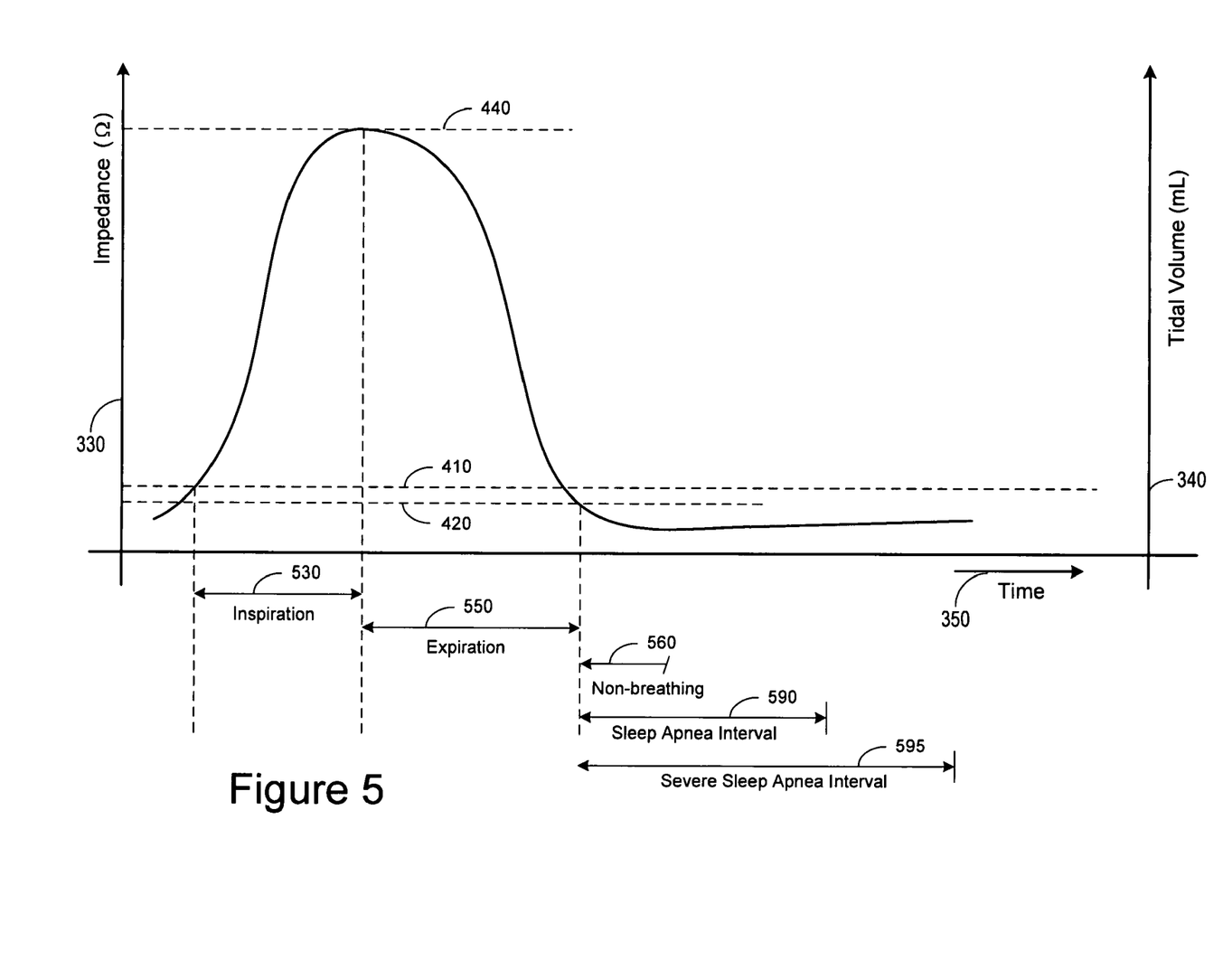
FIG. 5 is a graph of a respiration signal illustrating various intervals that may be used for detection of apnea in accordance with embodiments of the invention.
Figure 6:
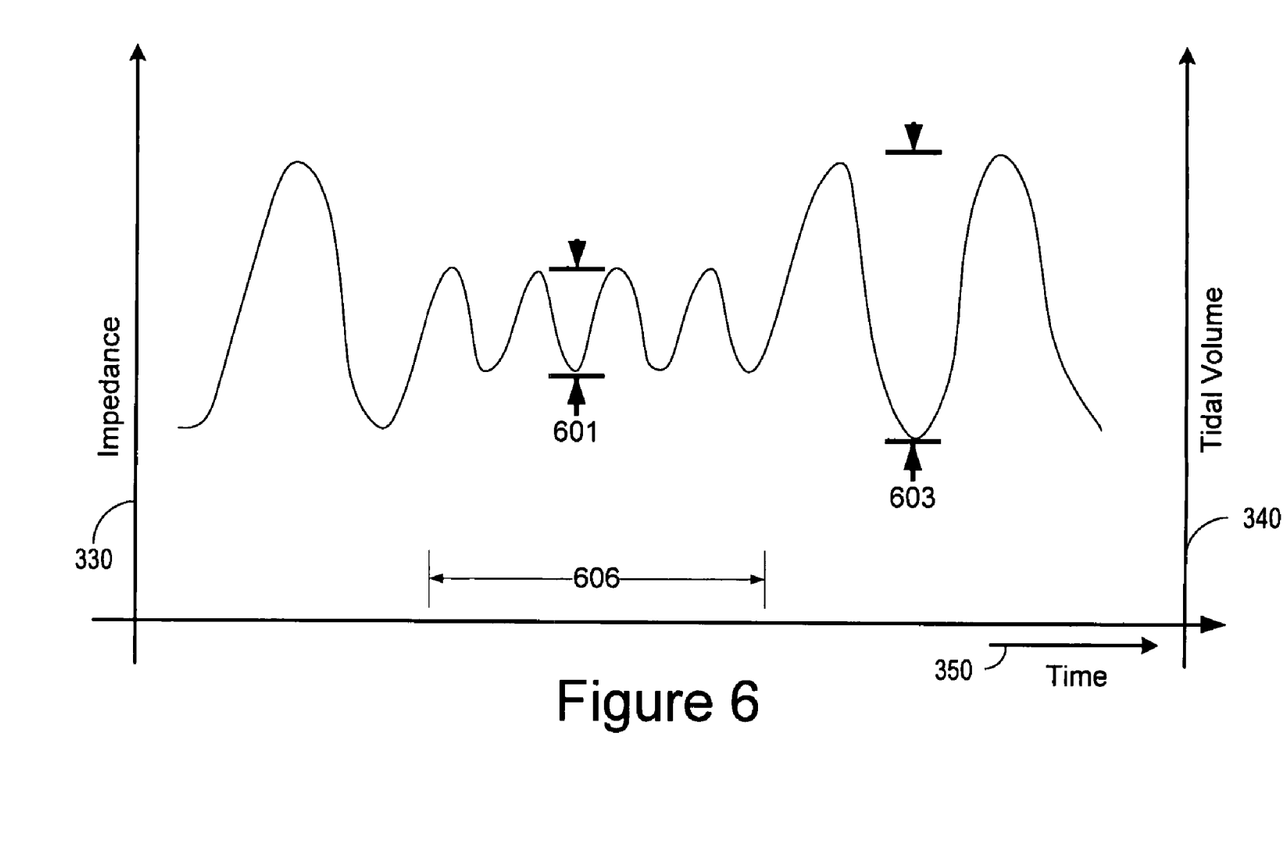
FIG. 6 is a respiration graph illustrating abnormally shallow respiration utilized in detection of disordered breathing in accordance with embodiments of the invention.

FIGS. 4-6 are graphs of transthoracic impedance and tidal volume, similar to FIG. 3 previously described. As in FIG. 3, FIGS. 4-6 illustrate the impedance signal 300 proportional to the transthoracic impedance, again illustrated as impedance 330 on the abscissa of the left side of the graphs versus time 350 on the ordinate of the graphs in FIGS. 4-6. The impedance 330 increases during any respiratory inspiration period 430 and decreases during any respiratory expiration period 450. As previously discussed, the impedance signal 300 is also proportional to the amount of air inhaled, denoted the tidal volume 340, illustrated on the abscissa of the right side of the graph in FIGS. 4-6. The magnitude of variations in impedance and tidal volume during respiration are identifiable as the peak-to-peak variation of the impedance signal 300.

FIG. 4 illustrates respiration intervals used for disordered breathing detection and/or prediction useful for determining or predicting blood oxygen and/or carbon dioxide saturation in accordance with embodiments of the present invention. Detection of disordered breathing may involve defining and examining a number of respiratory cycle intervals. A respiration cycle is divided into an inspiration period corresponding to the patient inhaling, an expiration period, corresponding to the patient exhaling, and a non-breathing period occurring between inhaling and exhaling. Respiration intervals are established using an inspiration threshold 410 and an expiration threshold 420. The inspiration threshold 410 marks the beginning of an inspiration period 430 and is determined by the transthoracic impedance signal 300 rising above the inspiration threshold 410. The inspiration period 430 ends when the transthoracic impedance signal 300 is a maximum 440. The maximum transthoracic impedance signal 440 corresponds to both the end of the inspiration interval 430 and the beginning of an expiration interval 450. The expiration interval 450 continues until the transthoracic impedance 300 falls below an expiration threshold 420. A non-breathing interval 460 starts from the end of the expiration period 450 and continues until the beginning of a next inspiration period 470.

Detection of sleep apnea and severe sleep apnea, conditions associated with low blood oxygen saturation and high carbon dioxide saturation, is illustrated in FIG. 5. The patient's respiration signals are monitored and the respiration cycles are defined according to an inspiration 530, an expiration 550, and a non-breathing 560 interval as described in connection with FIG. 4. A condition of sleep apnea is detected when a non-breathing period 560 exceeds a first predetermined interval 590, denoted the sleep apnea interval. A condition of severe sleep apnea is detected when the non-breathing period 560 exceeds a second predetermined interval 595, denoted the severe sleep apnea interval. For example, sleep apnea may be detected when the non-breathing interval exceeds about 10 seconds, and severe sleep apnea may be detected when the non-breathing interval exceeds about 20 seconds.

Hypopnea, another condition that can contribute to low blood oxygen saturation and high carbon dioxide saturation, is characterized by abnormally shallow breathing. FIG. 6 is a graph of tidal volume derived from transthoracic impedance measurements. The graph of FIG. 6 illustrating the tidal volume of a hypopnea episode may be compared to the tidal volume of a normal breathing cycle illustrated previously in FIG. 3, which illustrated normal respiration tidal volume and rate. As shown in FIG. 6, hypopnea involves a period of abnormally shallow respiration, possible at an increased respiration rate.

Hypopnea is detected by comparing a patient's respiratory tidal volume 603 to a hypopnea tidal volume 601. The tidal volume for each respiration cycle may be derived from transthoracic impedance measurements acquired in the manner described previously. The hypopnea tidal volume threshold may be established by, for example, using clinical results providing a representative tidal volume and duration of hypopnea events. In one configuration, hypopnea is detected when an average of the patient's respiratory tidal volume taken over a selected time interval falls below the hypopnea tidal volume threshold. Furthermore, various combinations of hypopnea cycles, breath intervals, and non-breathing intervals may be used to detect hypopnea, where the non-breathing intervals are determined as described above.

In FIG. 6, a hypopnea episode 606 is identified when the average tidal volume is significantly below the normal tidal volume. In the example illustrated in FIG. 6, the normal tidal volume during the breathing process is identified as the peak-to peak value identified as the respiratory tidal volume 603. The hypopnea tidal volume during the hypopnea episode 606 is identified as hypopnea tidal volume 601. For example, the hypopnea tidal volume 601 may be about 50% of the respiratory tidal volume 603. The value 50% is used by way of example only, and determination of thresholds for hypopnea events may be determined as any value appropriate for a given patient.

In the example above, if the tidal volume falls below 50% of the respiratory tidal volume 603, the breathing episode may be identified as a hypopnea event, originating the measurement of the hypopnea episode 606.

Disordered breathing detection and prediction systems and methods that can benefit from or otherwise incorporate features of the present invention are further described in U.S. patent application Ser. No. 10/309,771 filed Dec. 4, 2002; Ser. No. 10/309,770 filed Dec. 4, 2002; and Ser. No. 10/643,016 filed Aug. 18, 2003, all of which are hereby incorporated by reference herein.

Figure 7:
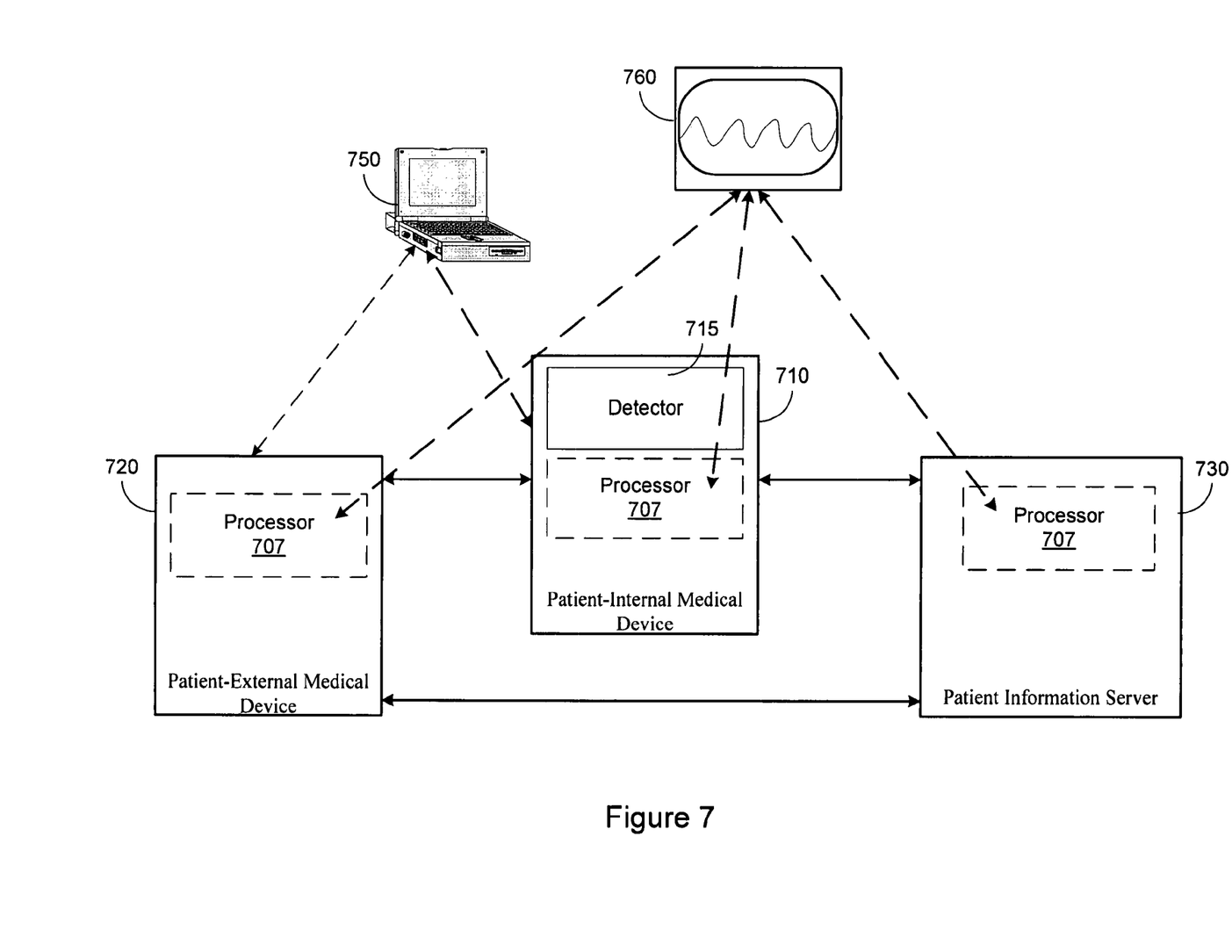
FIG. 7 is a block diagram of a medical system that may incorporate blood gas prediction devices used in accordance with embodiments of the invention.

FIG. 7 is a block diagram illustrating components of a system 700 for measuring parameters indicative of blood oxygen and/or carbon dioxide saturation in accordance with principles of the present invention. In accordance with embodiments of the invention, the system illustrated in FIG. 7 includes a patient internal medical device 710, a patient external medical device 720, and a patient information server 730.

Patient internal medical device 710 includes a detector 715 that implantably detects and measures respiratory characteristics. The patient-internal medical device 710 may be a fully or partially implantable device that performs monitoring, diagnosis, and/or therapy functions.

The patient-external medical device 720 may perform monitoring, diagnosis and/or therapy functions external to the patient (i.e., not invasively implanted within the patient's body). The patient-external medical device 720 may be positioned on the patient, near the patient, or in any location external to the patient. It is understood that a portion of a patient-external medical device 720 may be positioned within an orifice of the body, such as the nasal cavity or mouth, yet can be considered external to the patient (e.g., mouth pieces/appliances, tubes/appliances for nostrils, or temperature sensors positioned in the ear canal).

A processor 707 can be incorporated in any of the patient internal medical device 710, patient external medical device 720 or patient information server 730 and operates to measure blood oxygen and/or carbon dioxide saturation in accordance with principles of the present invention. Processor 707 can be configured as a network processor in certain implementations. Processor 707 can determine the magnitude and/or frequency of change in a patient's transthoracic impedance. For example, processor 707 measures a decrease in blood oxygen saturation and/or an increase in blood carbon dioxide saturation when a patient's detected respiratory characteristic such as respiratory tidal volume, minute ventilation, and respiratory rate decrease. Similarly, processor 707 measures a decrease in blood oxygen saturation and increase in blood carbon dioxide saturation when detecting an increased occurrence of sleep disordered breathing.

Detector 715 provided in patient internal medical device 710 can be wirelessly coupled to any of the patient external medical device 720 and/or patient information server 730 in order to communicate respiratory parameter information to processor 707, or to any other device that can use the information generated by detector 715.

Detector 715 may be coupled to processor 707 and to patient-internal medical device 710 when situated within the patient-internal medical device 710 through implanted leads. In one example, an internal endocardial lead system is used to couple sensing electrodes to an implantable pacemaker or other cardiac rhythm management device. One or more of detectors 715 can be equipped with transceiver circuitry to support wireless communication between the one or more patient-internal sensors (not shown) and the patient-internal medical device 710 and/or the patient-external medical device 720.

The medical devices 710, 720 may be coupled to one or more patient-input devices 750. The patient-input devices 750 facilitate manual transfer of information to the medical devices 710, 720 by the patient. The patient input devices 750 may be particularly useful for inputting information concerning patient perceptions, such as a patient's activity level, whether the patient is awake, patient smoking or drug use, for example.

The patient-internal medical device 710 and the patient-external medical device 720 may be coupled through a wireless or wired communications link to a patient information server 730. The patient information server 730 may be used to download and store data collected by the patient-internal and patient-external medical devices 710, 720. Alternatively, information generated by detector 715 and/or processor 707 can be stored in any of the patient internal medical device 710 and patient external medical device 720 for future use.

In further embodiments of the invention, a display device 760 can be communicatively coupled to the processor 707 in order to display information related to a patient's condition including a change in blood oxygen and/or carbon dioxide saturation. This allows a patient's physician to access patient data transmitted from the processor 707. After evaluation of the patient data, the patient's physician may communicate with one or more of the patient-internal or patient-external devices 710, 720 through a patient information server 730 such as an advanced patient management (APM) system to initiate, terminate, or modify the monitoring, diagnostic, and/or therapy functions of the patient-internal and/or patient-external medical systems 710, 720. Systems and methods involving advanced patient management techniques are further described in U.S. Pat. Nos. 6,336,903, 6,312,378, 6,270,457, and 6,398,728 which are incorporated by reference herein in their entirety.

Figure 8:
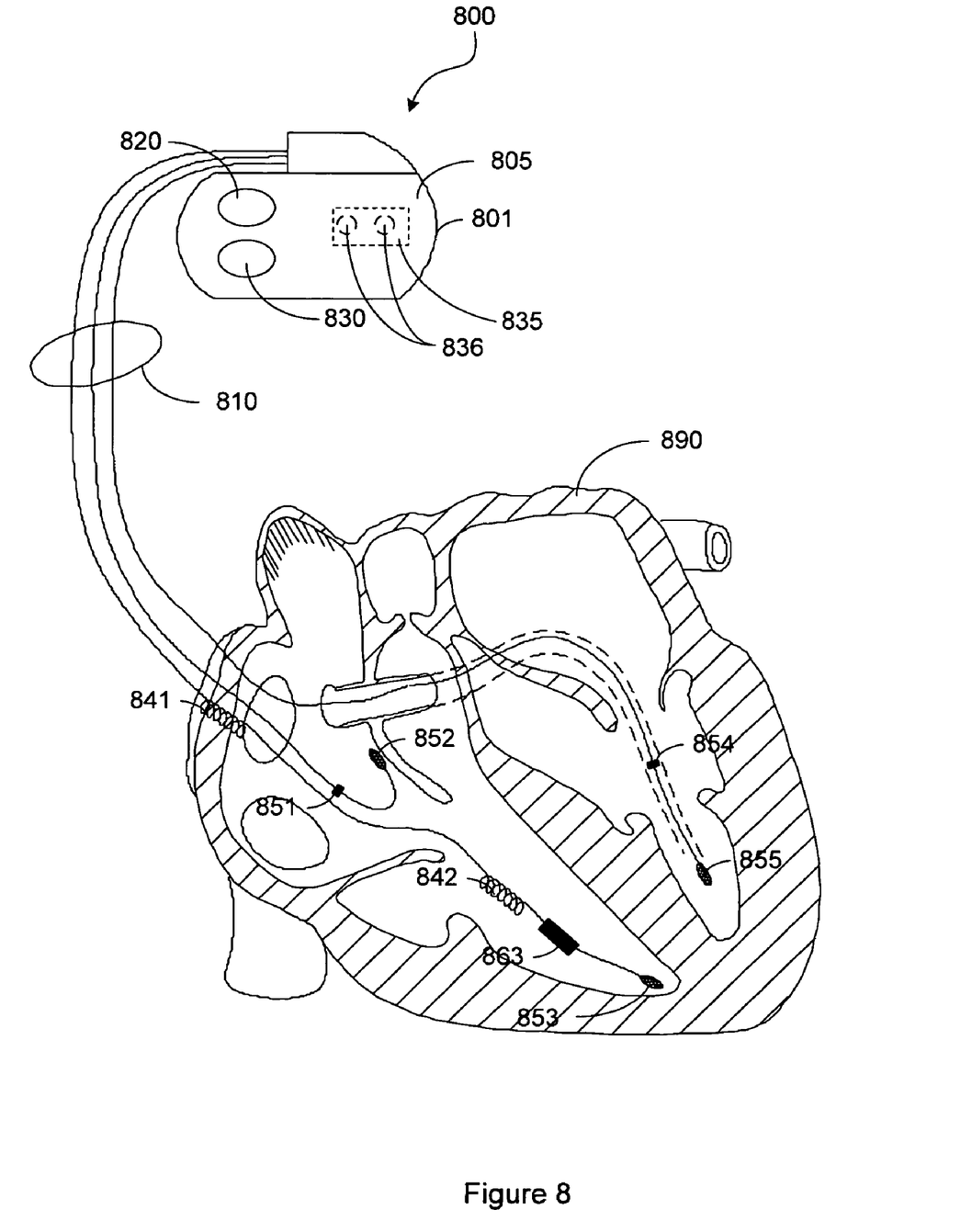
FIG. 8 is a partial view of an implantable device that may include circuitry for implementing a detector for measuring blood gas saturation in accordance with embodiments of the invention.

FIG. 8 is a partial view of an implantable device that may include circuitry for implementing blood oxygen and/or carbon dioxide saturation detection for measuring blood oxygen and/or carbon dioxide levels in the blood in accordance with embodiments of the invention. In this example, the implantable device comprises a cardiac rhythm management device (CRM) 800 including an implantable pulse generator 805 electrically and physically coupled to an intracardiac lead system 810. A blood oxygen and/or carbon dioxide saturation detection system of the present invention may alternatively be implemented in a variety of implantable monitoring, diagnostic, and/or therapeutic devices, such as an implantable cardiac monitoring device, an implantable drug delivery device, or an implantable neurostimulation device, for example.

Portions of the intracardiac lead system 810 are inserted into the patient's heart 890. The intracardiac lead system 810 includes one or more electrodes configured to sense electrical cardiac activity of the heart, deliver electrical stimulation to the heart, sense the patient's transthoracic impedance, and/or sense other physiological parameters, e.g., cardiac chamber pressure or temperature. Portions of the housing 801 of the pulse generator 805 may optionally serve as a can electrode.

Communications circuitry is disposed within the housing 801 for facilitating communication between the pulse generator 805 and an external communication device, such as a portable or bed-side communication station, patient-carried/worn communication station, or external programmer, for example. The communications circuitry can also facilitate unidirectional or bidirectional communication with one or more implanted, external, cutaneous, or subcutaneous physiologic or non-physiologic sensors, patient-input devices and/or information systems.

The pulse generator 805 may optionally incorporate a motion detector 820 that may be used to sense various respiration-related conditions. For example, the motion detector 820 may be optionally configured to sense snoring, activity level, and/or chest wall movements associated with respiratory effort, for example. The motion detector 820 may be implemented as an accelerometer positioned in or on the housing 801 of the pulse generator 805. If the motion sensor is implemented as an accelerometer, the motion sensor may also provide the sensing of respiratory, e.g. rales, coughing, rate, and cardiac, e.g. S1-S4 heart sounds, murmurs, and other acoustic information. Information generated from an accelerometer (e.g., posture, activity) can be used in certain embodiments of the present invention with measured respiratory parameters for enhancing blood oxygen and/or carbon dioxide saturation determinations.

The pulse generator 805 may optionally incorporate a pressure sensor that may be used to sense various respiration-related conditions. A pressure sensor may be used to infer respiration. A pressure sensor, which may be depicted by one or more of elements 851, 854, and 863 in FIG. 8, may be optionally configured to sense sleep disordered breathing, such as central apnea or obstructive apnea, or to discriminate between various types of sleep disordered breathing. The pressure sensor may be implemented as a sensor positioned in or on the lead of lead system 810. The pressure sensor may be used to provide sensing of other physiological signals, such as systolic pressure, diastolic pressure, pulmonary artery pressure, left atrial pressure, etc. Information generated from the pressure sensor(s) can be used in certain embodiments of the present invention to measure respiratory parameters for determining blood oxygen and carbon dioxide saturation.

The lead system 810 of the CRM 800 may incorporate one or more transthoracic impedance sensors that may be used to acquire the patient's respiration waveform, or other respiration-related information. The transthoracic impedance sensor may include, for example, one or more intracardiac electrodes 841, 842, 851-855, 863 positioned in one or more chambers of the heart 890. The intracardiac electrodes 841, 842, 851-855, 863 may be coupled to impedance drive/sense circuitry 830 positioned within the housing of the pulse generator 805.

The lead system 810 may include one or more leads each having one or more electrodes that extend into the heart. FIG. 8 shows three such leads, one that extends into the right atrium, one that extends into the right ventricle, and one that extends into a coronary vein for placement at the surface of the left ventricle. The left ventricular lead, in particular, includes an LV distal electrode 855 and an LV proximal electrode 854 located at appropriate locations in or about the left ventricle for pacing and/or sensing the left ventricle. The left ventricular lead may be guided into the right atrium of the heart via the superior vena cava. From the right atrium, the left ventricular lead may be deployed into the coronary sinus ostium, the opening of the coronary sinus. The lead may be guided through the coronary sinus to a coronary vein of the left ventricle. This vein is used as an access pathway for leads to reach the surfaces of the left ventricle that are not directly accessible from the right side of the heart.

In one implementation, impedance drive/sense circuitry 830 generates a current that flows through the tissue between an impedance drive electrode 851 and a can electrode on the housing 801 of the pulse generator 805, which can be used in determining blood oxygen and/or carbon dioxide saturation in accordance with embodiments of the invention. The voltage at an impedance sense electrode 852 relative to the can electrode changes as the patient's transthoracic impedance changes. The voltage signal developed between the impedance sense electrode 852 and the can electrode is detected by the impedance sense circuitry 830. Other locations and/or combinations of impedance sense and drive electrodes are also possible.

The voltage signal developed at the impedance sense electrode 852, illustrated previously in FIG. 3, is proportional to the patient's transthoracic impedance and represents the patient's respiration waveform. The transthoracic impedance increases during respiratory inspiration 320 and decreases during respiratory expiration 310. The peak-to-peak transition of the transthoracic impedance is proportional to the amount of air moved in one breath, denoted the tidal volume. The amount of air moved per minute is denoted the minute ventilation. A normal "at rest" respiration pattern, e.g., during non-REM sleep, includes regular, rhythmic inspiration-expiration cycles without substantial interruptions, as indicated previously in FIG. 3. Abnormal transthoracic impedance patterns are illustrated in FIGS. 5-6 described above and can be used to determine blood oxygen and/or carbon dioxide saturation in accordance with embodiments of the invention.

Returning to FIG. 8, the lead system 810 may include one or more cardiac pace/sense electrodes 851-855 positioned in, on, or about one or more heart chambers for sensing electrical signals from the patient's heart 890 and/or delivering pacing pulses to the heart 890. The intracardiac sense/pace electrodes 851-855, such as those illustrated in FIG. 8, may be used to sense and/or pace one or more chambers of the heart, including the left ventricle, the right ventricle, the left atrium and/or the right atrium. The lead system 810 may include one or more defibrillation electrodes 841, 842 for delivering defibrillation/cardioversion shocks to the heart.

The pulse generator 805 may include circuitry for detecting cardiac arrhythmias and/or for controlling pacing or defibrillation therapy in the form of electrical stimulation pulses or shocks delivered to the heart through the lead system 810. Circuitry for measuring blood oxygen and/or carbon dioxide levels by implementing a blood oxygen and/or carbon dioxide saturation detector 835, including interface circuitry, a respiratory parameter detector, a processor, and/or memory circuitry, as described in connection with the FIG. 7, may be housed within the pulse generator 805. The blood oxygen and/or carbon dioxide saturation detector circuitry may be coupled to various sensors, patient input devices, and/or information systems through leads or through wireless communication links. In addition, blood oxygen and/or carbon dioxide saturation detector 835 may be incorporated as a component or function of a processor, such as processor 707 illustrated in FIG. 7.

In another implementation, one or more EMG sensors 836 may be placed on the housing, header, or lead of CRM 800. In this configuration, the EMG sensors 836 may be used to detect atonia of the pectoral muscles during REM sleep. A sleep detector may use information from the EMG sensors 836 to facilitate the detection of sleep onset and offset, and to determine the various stages of sleep. Detection of sleep stages may be used, for example, in patient monitoring, diagnosis and/or therapy for various disorders, including sleep disordered breathing. Techniques involving EMG sensors 836 positioned on CRM device 800, for example, are described in commonly owned U.S. patent application Ser. No. 10/643,006, filed Aug. 18, 2003, entitled "Sleep State Classification," which is incorporated by reference herein in its entirety.

Figure 9:
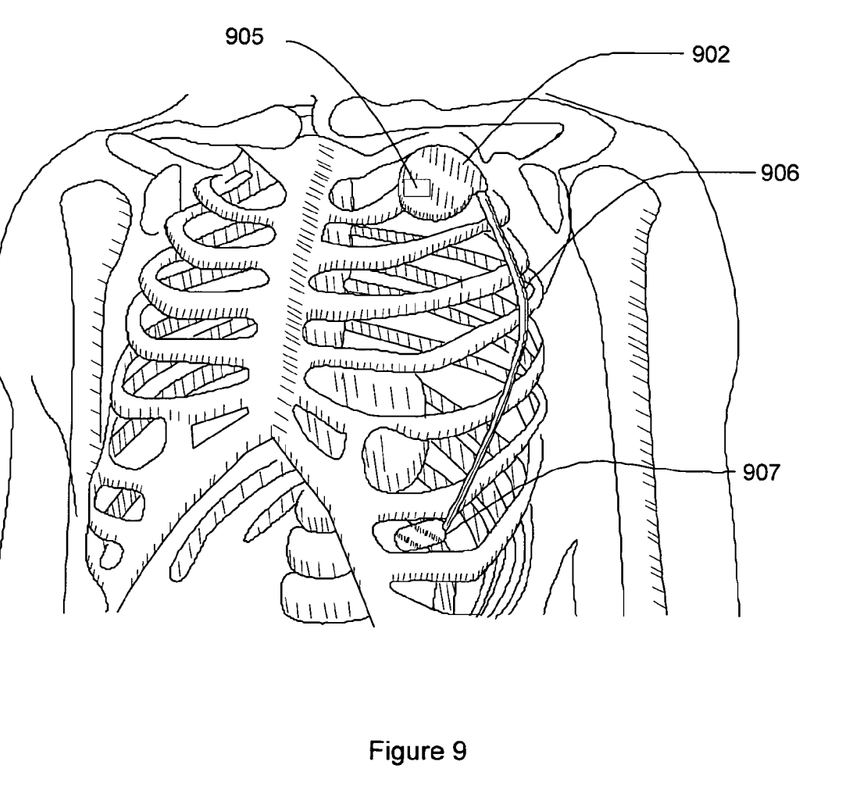
FIG. 9 is a diagram illustrating an implantable transthoracic cardiac device that may be used in connection with acquiring and organizing data for a blood gas saturation detector for measuring levels of oxygen and carbon dioxide in blood in accordance with embodiments of the invention.

FIG. 9 is a diagram illustrating an implantable transthoracic cardiac device that may be used in connection with acquiring and organizing data for measuring of blood oxygen and/or carbon dioxide saturation in accordance with embodiments of the invention. The implantable device illustrated in FIG. 9 is an implantable transthoracic cardiac sensing and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for sensing cardiac and respiratory activity and delivering cardiac stimulation therapy. It is understood that elements of the ITCS device may be located at several different body locations, such as in the chest, abdominal, or subclavian region with electrode elements respectively positioned at different regions near, around, in, or on the heart.

In the configuration shown in FIG. 9, a subcutaneous electrode assembly 907 can be positioned under the skin in the chest region and situated distal from the housing 902. The subcutaneous and, if applicable, housing electrode(s) can be positioned about the heart at various locations and orientations, such as at various anterior and/or posterior locations relative to the heart. The subcutaneous electrode assembly 907 is coupled to circuitry within the housing 902 via a lead assembly 906. One or more conductors (e.g., coils or cables) are provided within the lead assembly 906 and electrically couple the subcutaneous electrode assembly 907 with circuitry in the housing 902. One or more sense, sense/pace or defibrillation electrodes can be situated on the elongated structure of the electrode support, the housing 902, and/or the distal electrode assembly (shown as subcutaneous electrode assembly 907 in the configuration shown in FIG. 9).

The housing 902 (e.g., the active or non-active can) of the ITCS device, for example, may be configured for positioning outside of the rib cage at an intercostal or subcostal location, within the abdomen, or in the upper chest region (e.g., subclavian location, such as above the third rib). In one implementation, one or more electrodes may be located on the primary housing and/or at other locations about, but not in direct contact with the heart, great vessel or coronary vasculature.

In particular configurations, the ITCS device may perform functions traditionally performed by cardiac rhythm management devices, such as providing various cardiac monitoring, pacing and/or cardioversion/defibrillation functions. Exemplary pacemaker circuitry, structures and functionality, aspects of which can be incorporated in an ITCS device of a type that may benefit from multi-parameter sensing configurations, are disclosed in commonly owned U.S. Pat. Nos. 4,562,841; 5,284,136; 5,376,476; 5,036,849; 5,540,727; 5,836,987; 6,044,298; and 6,055,454, which are hereby incorporated herein by reference in their respective entireties. It is understood that ITCS device configurations can provide for non-physiologic pacing support in addition to, or to the exclusion of, bradycardia and/or anti-tachycardia pacing therapies. Exemplary cardiac monitoring circuitry, structures and functionality, aspects of which can be incorporated in an ITCS of the present invention, are disclosed in commonly owned U.S. Pat. Nos. 5,313,953; 5,388,578; and 5,411,031, which are hereby incorporated herein by reference in their respective entireties.

An ITCS device can incorporate circuitry, structures and functionality of the subcutaneous implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243 and commonly owned U.S. patent applications "Subcutaneous Cardiac Sensing, Stimulation, Lead Delivery, and Electrode Fixation Systems and Methods," Ser. No. 60/462,272, filed Apr. 11, 2003, and Hybrid Transthoracic/Intrathoracic Cardiac Stimulation Devices and Methods," Ser. No. 10/462,001, filed Jun. 13, 2003, and "Methods and Systems Involving Subcutaneous Electrode Positioning Relative to A Heart," Ser. No. 10/465,520, filed Jun. 19, 2003, and "Reconfigurable Implantable Cardiac Monitoring and Therapy Delivery Device," Ser. No. 10/785,431, filed on Feb. 24, 2004, and "Reconfigurable Subcutaneous Cardiac Device," Ser. No. 10/821,248, filed Apr. 8, 2004, which are incorporated by reference.

Circuitry for implementing blood oxygen and/or carbon dioxide saturation detection, in accordance with embodiments of the invention, may be positioned within the primary housing 902 as a blood oxygen and/or carbon dioxide saturation detector 905 or may be incorporated as a component or function of a processor within the primary housing 902 of the ITCS device. In one example, circuitry for implementing blood oxygen and/or carbon dioxide saturation detection may include an impedance sensor configured to sense the patient's transthoracic impedance in order to detect respiratory parameters that can be used to measure blood oxygen and/or carbon dioxide saturation. The impedance sensor may include the impedance drive/sense circuitry incorporated with the housing 902 of the ITCS device or the blood oxygen and/or carbon dioxide saturation detector 905 and may be coupled to impedance electrodes positioned on the can or at other locations of the ITCS device, such as on the subcutaneous electrode assembly 907 and/or lead assembly 906.

In one configuration, the impedance drive circuitry generates a current that flows between a subcutaneous impedance drive electrode and a can electrode on the primary housing of the ITCS device. The voltage at a subcutaneous impedance sense electrode relative to the can electrode changes as the patient's transthoracic impedance changes. The voltage signal developed between the impedance sense electrode and the can electrode is sensed by the impedance drive/sense circuitry.

Communications circuitry is disposed within the housing 902 and/or within blood oxygen saturation detector 905 for facilitating communication between the ITCS device and an external communication device, such as a portable or bedside communication station, patient-carried/worn communication station, or external programmer, for example. The communications circuitry can also facilitate unidirectional or bidirectional communication with one or more external, cutaneous, or subcutaneous physiologic or non-physiologic sensors.

The present invention is capable of measuring oxygen and/or carbon dioxide saturation without the use of oxygen or carbon dioxide sensors, which may be problematic for reasons previously discussed. Furthermore, the ability to predict blood oxygen and/or carbon dioxide saturation may better align the results of cardiac device-based disordered breathing detection algorithm with in-lab polysomnography, allowing for a better understanding of patient conditions. It should be understood that embodiments of the present invention are directed not only towards determining blood oxygen and/or carbon dioxide saturation levels using a parameter of respiration as a basis for the determination, but are also directed towards determining blood oxygen and/or carbon dioxide saturation based on a combination of respiratory parameters.

A number of the examples presented herein involve block diagrams illustrating functional blocks used for coordinated monitoring, diagnosis and/or therapy functions in accordance with embodiments of the present invention. It will be understood by those skilled in the art that there exist many possible configurations in which these functional blocks may be arranged and implemented. The examples depicted herein provide examples of possible functional arrangements used to implement the approaches of the invention.

Each feature disclosed in this specification (including any accompanying claims, abstract, and drawings) may be replaced by alternative features having the same, equivalent or similar purpose, unless expressly stated otherwise. Thus, unless expressly stated otherwise, each feature disclosed is one example only of a generic series of equivalent or similar features.

Various modifications and additions can be made to the preferred embodiments discussed hereinabove without departing from the scope of the present invention. Accordingly, the scope of the present invention should not be limited by the particular embodiments described above, but should be defined only by the claims set forth below and the equivalents thereof.

What is claimed is:

1. A method for measuring parameters indicative of blood gas saturation, comprising:
   implantably measuring a parameter of respiration over a duration of time;
   associating the measured respiratory parameter with a blood gas saturation level; and
   determining blood gas saturation based on the measured respiration parameter.

2. The method of claim 1, wherein the blood gas saturation comprises blood oxygen saturation.

3. The method of claim 1, wherein the blood gas saturation comprises blood carbon dioxide saturation.

4. The method of claim 1, wherein at least one of associating the measured respiratory parameter and determining blood gas saturation is performed implantably.

5. The method of claim 1, wherein the parameter of respiration comprises one or both of a magnitude and a frequency of change in transthoracic impedance.

6. The method of claim 1, wherein the parameter of respiration comprises at least one of a respiration pattern, a respiration interval, tidal volume, and minute ventilation.

7. The method of claim 1, wherein the parameter of respiration comprises at least one of a duration of an apnea episode, a duration of a hypopnea episode, and a duration of a Cheyne-Stokes respiration episode.

8. The method of claim 1, wherein the parameter of respiration comprises at least one of a hyperventilation duration after an apnea episode, hypopnea episode, or a Cheyne-Stokes respiration episode.

9. The method of claim 1, wherein the parameter of respiration comprises a frequency of respiration during a disordered breathing event.

10. The method of claim 1, wherein the parameter of respiration comprises a frequency of respiration before or after a disordered breathing event.

11. The method of claim 1, wherein implantably measuring the parameter of respiration comprises implantably measuring a baseline parameter of respiration during patient wakefulness.

12. The method of claim 1, wherein determining blood gas saturation comprises determining blood gas saturation during sleep.

13. The method of claim 1, further comprising:
   detecting sleep disordered breathing; and
   indicating a severity level of the sleep disordered breathing in response to detecting sleep disordered breathing with a presence or absence of a change in blood gas saturation.

14. The method of claim 1, further comprising:
   measuring one or more of a cardiac parameter, blood pressure parameter and blood flow parameter; and
   wherein determining the blood gas saturation is further based at least in part on one or more of the cardiac parameter, blood pressure parameter and blood flow parameter.

15. The method of claim 1, wherein determining blood gas saturation further comprises indicating a decrease in blood oxygen saturation in response to measuring a decrease in at least one of a respiratory tidal volume, a minute ventilation, and a respiration rate.

16. The method of claim 1, wherein determining blood gas saturation further comprises indicating an increase in blood carbon dioxide saturation in response to measuring a decrease in at least one of a respiratory tidal volume, a minute ventilation, and a respiration rate.

17. The method of claim 1, wherein determining blood gas saturation comprises indicating a decrease in blood oxygen saturation in response to measuring an increase in sleep disordered breathing episodes.

18. The method of claim 1, wherein determining blood gas saturation comprises indicating an increase in blood carbon dioxide saturation in response to measuring an increase in sleep disordered breathing episodes.

19. A system for measuring parameters indicative of blood gas saturation, comprising:
   an implantable device configured to measure a parameter of respiration over a duration of time; and a processor configured to associate the measured respiratory parameter with a blood gas saturation level, and to determine blood gas saturation based on the measured respiration parameter.

20. The system of claim 19, wherein the processor is configured to detect one or both of a magnitude and frequency of change in transthoracic impedance.

21. The system of claim 19, wherein the processor is disposed in an implantable housing.

22. The system of claim 19, further comprising:
a sensor configured to measure a cardiac parameter, wherein the processor is configured to associate the cardiac parameter with a blood gas saturation level, and to determine blood gas saturation based at least in part on the measured cardiac parameter.

23. The system of claim 19, further comprising:
a sensor configured to measure a blood pressure parameter, and
wherein the processor is configured to associate the blood pressure parameter with a blood gas saturation level, and to determine blood gas saturation based at least in part on the measured blood pressure parameter.

24. The system of claim 19, further comprising:
a sensor configured to measure a blood flow parameter, and
wherein the processor is configured to associate the blood flow parameter with a blood gas saturation level, and to determine blood gas saturation based at least in part on the measured blood flow parameter.

25. The system of claim 14, further comprising:
a sensor configured to measure one or both of patient activity and patient posture, and
wherein the processor is configured to determine or confirm blood gas saturation based at least in part on the measured one or both of patient activity and patient posture.

26. The system of claim 14, further comprising a communication link configured to communicate the determined blood gas saturation values to a patient-external location.

27. A system for measuring parameters indicative of blood gas saturation, comprising:
means for implantably measuring a parameter of respiration over a duration of time;
means for associating the measured respiratory parameter with a blood gas saturation level; and
means for determining blood gas saturation based on the measured respiration parameter.

* * * * *